United States Patent

Tsuda et al.

[11] 4,076,821
[45] Feb. 28, 1978

[54] 4,4-DIPHENYLCYCLOALKYLPIPERIDINES AND PSYCHOTROPIC COMPOSITIONS THEREOF

[75] Inventors: Yoshinao Tsuda, Fukuoka; Masafumi Arita, Nakatsu; Toshio Hamasaki, Nakatsu; Tatsumi Tsumagari, Nakatsu; Takenori Kenjo, Fukuoka, all of Japan

[73] Assignee: Yoshitomi Pharmaceutical Industries, Ltd., Osaka, Japan

[21] Appl. No.: 662,197

[22] Filed: Feb. 27, 1976

[51] Int. Cl.$^2$ .......................................... C07D 401/04
[52] U.S. Cl. .................... 424/263; 260/293.6; 260/293.66; 260/293.75; 260/293.76; 260/293.8; 260/293.84; 260/295 K; 260/456 P; 260/590 C; 260/649 DP; 424/267
[58] Field of Search ...................... 260/293.61, 293.66, 260/293.84, 295 K, 293.6; 424/263, 267

[56] References Cited
U.S. PATENT DOCUMENTS

| | | | |
|---|---|---|---|
| 3,542,729 | 11/1970 | Murayama et al. | 260/45.8 |
| 3,639,409 | 2/1972 | Murayama et al. | 260/293.66 |
| 3,839,341 | 10/1974 | Scharpf et al. | 260/293.66 |
| 3,864,348 | 2/1975 | Regnier et al. | 260/293.66 |
| 3,989,707 | 6/1974 | Janssen et al. | 260/293.6 |

*Primary Examiner*—Henry R. Jiles
*Assistant Examiner*—Richard A. Schwartz
*Attorney, Agent, or Firm*—Sughrue, Rothwell, Mion, Zinn & Macpeak

[57] ABSTRACT

4,4-Diphenylcyclohexylpiperidine compounds and their analogs of the formula:

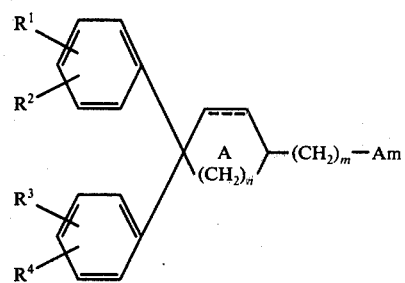

wherein the dotted line in Ring A indicates an optional bond; $R^1$, $R^2$, $R^3$ and $R^4$ are independently a hydrogen atom, a halogen atom, a trifluoromethyl group or a lower alkyl group; $n$ is 1 or 2; $m$ is 0 or 1; and Am is a piperidino group of the formula:

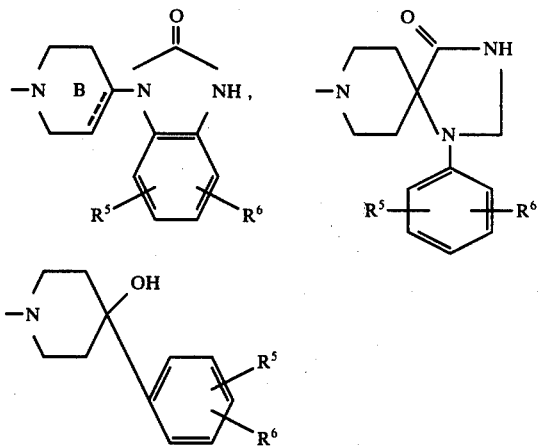

where
$R^5$ and $R^6$ are independently a hydrogen atom, a halogen atom, a trifluoromethyl group or a lower alkyl group, and the dotted line in Ring B indicates an optional bond;

and pharmaceutically acceptable salts thereof are disclosed. They exhibit potent and long-lasting psychotropic effects.

52 Claims, No Drawings

4,4-DIPHENYLCYCLOALKYLPIPERIDINES AND PSYCHOTROPIC COMPOSITIONS THEREOF

This invention relates to novel 4,4-diphenylcyclohexylpiperidine compounds and their analogs of the formula:

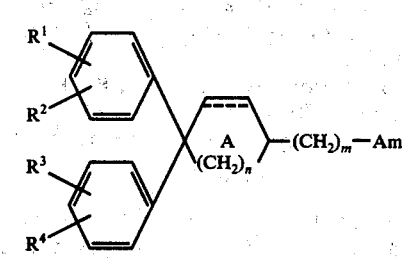

(I)

wherein:
the dotted line in Ring A indicates an optional bond;
$R^1$, $R^2$, $R^3$ and $R^4$ are independently a hydrogen atom, a halogen atom (e.g. F, Cl, Br or I), a trifluoromethyl group or a lower alkyl group (e.g. methyl, ethyl, propyl, isopropyl, butyl, sec-butyl or pentyl);
$n$ is 1 or 2;
$m$ is 0 or 1;
Am is a piperidino group of the formula:

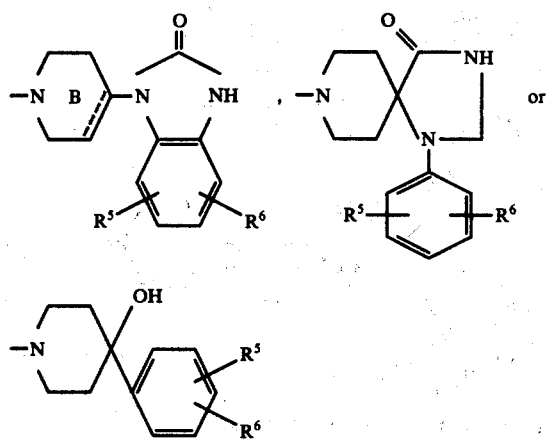

where the dotted line in Ring B indicates an optional bond; and $R^5$ and $R^6$ are independently a hydrogen atom, a halogen atom, a trifluoromethyl group or a lower alkyl group; and pharmaceutically acceptable acid addition and quaternary ammonium salts thereof, pharmaceutical compositions containing the said compounds and the use thereof.

Preferred classes of compounds (I) are those wherein $R^1$ is F, $R^2$ is H or F, $R^3$ is F, $R^4$ is H or F, $n$ is 2, and $m$ is 0.

The compounds of formula (I) can be produced by one of the following methods:

METHOD I

Reaction of a compound of the formula:

(II)

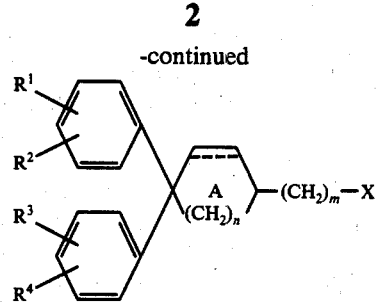

with a compound of the formula:

$$H - Am \quad (III)$$

wherein $R^1$, $R^2$, $R^3$, $R^4$, $n$, $m$, the dotted line in Ring A and Am are as defined above, and X is a reactive atom or group such as a halogen atom (e.g. Cl, Br or I) or an organic sulfonyloxy group (e.g. mesyloxy or tosyloxy).

The reaction is usually carried out in an inert solvent such as methanol, ethanol, acetone, methyl ethyl ketone, tetrahydrofuran, dioxane, methylene chloride, chloroform, benzene, toluene, xylene, dimethylformamide, dimethyl sulfoxide, hexamethylphosphoric triamide or N-methylpyrrolidone or a mixture thereof, in the presence of an acid acceptor such as potassium carbonate, sodium carbonate, sodium hydrogen carbonate, calcium hydrogen carbonate, sodium hydroxide, potassium hydroxide, sodium methoxide, sodium ethoxide, sodium tert-butoxide, sodium acetate, potassium acetate, pyridine or triethylamine, if desired in the presence of a catalyst such as potassium iodide, at a temperature of from about 40° C to about 90° C, for a period of from about 30 minutes to about 100 hours.

METHOD II

This method, to be applied for the production of compounds of formula (I) wherein $m$ is 0, comprises subjecting to dehydration reaction a compound of the formula:

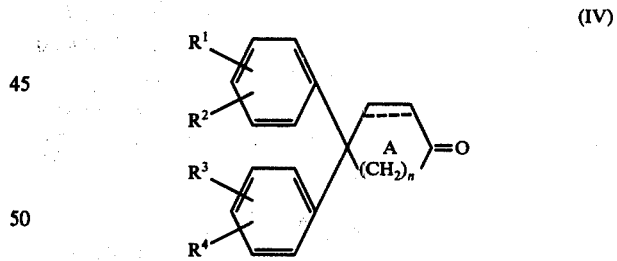

(IV)

with a compound of formula (III), and subjecting to reduction the resulting compound of the formula:

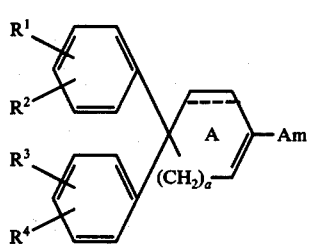

(V)

wherein $R^1$, $R^2$, $R^3$, $R^4$, $n$, the dotted line in Ring A and Am are as defined above, and $a$ is 0 or 1.

The dehydration reaction is usually carried out in an inert solvent such as mentioned for Method I, preferably benzene, toluene or xylene, in the presence of an acid catalyst such as hydrogen chloride, sulfuric acid or p-toluenesulfonic acid, at a temperature of from room temperature to a boiling point of the solvent employed, for a period of from several hours to several days.

The emanine intermediate of formula (V) can be isolated and purified by a conventional method such as distillation, recrystallization or chromatography. The isolation is, however, not always necessary.

The reduction includes catalytic and chemical reductions. The catalytic reduction is carried out over a metal (e.g. palladium, platinum, rhodium, nickel, ruthenium or cobalt) on a carrier (e.g. active carbon, alumina, barium sulfate, calcium carbonate or strontium carbonate), in an inert solvent such as mentioned for Method I. The reaction time is dependent on reaction conditions such as pressure and temperature, and many hours are required at room temperature and atmospheric pressure. The chemical reduction is carried out by the use of formic acid (or its derivative) or a complex metal hydride. The reduction by the use of formic acid is usually carried out by adding formic acid to a compound of formula (V), and maintaining the resulting mixture at an elevated temperature. The reduction by the use of a complex metal hydride is carried out in an inert solvent such as mentioned for Method I, a a temperature of from 0° C to a boiling point of the solvent employed, for a period of from several minutes to 10 hours. The complex metal hydride includes, for example, lithium aluminum hydride, sodium borohydride, boron hydride (borane) and $NaAl(OCH_2CH_2OCH_3)_2H_2$, and a combination of, for example, lithium aluminum hydride - aluminum chloride or sodium borohydride - aluminum chloride may also be used. In case a double bond is existent in Ring A or B, the chemical reduction is preferred.

The compounds of formula (I) can also be produced by one of the following methods III to V, however, from the economical point of view, they are not so advantageous as Methods I and II as mentioned above.

METHOD III

This method, to be applied for the production of compounds of formula (I) wherein Am is the group of the formula:

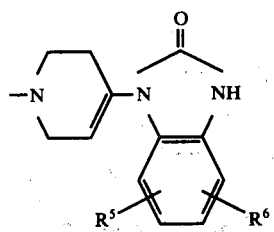

and m is 0, comprises reacting a compound of the formula:

(VI)

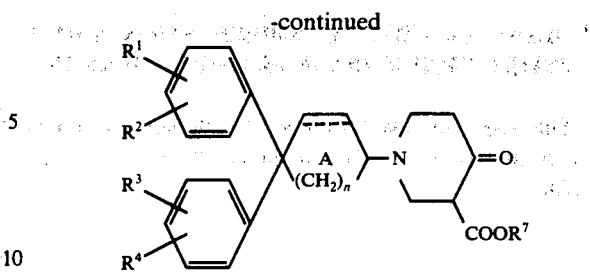

with a compound of the formula:

(VII)

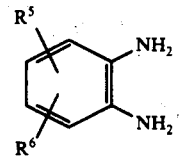

in an inert solvent having a relatively high boiling point such as benzene or xylene, at about 80° C to about 200° C for 5 to 24 hours.

In the above formulas, $R^1$, $R^2$, $R^3$, $R^4$, $R^5$, $R^6$, n and the dotted line in Ring A are as defined above, and $R^7$ is a lower alkyl group (preferably methyl or ethyl).

METHOD IV

This method, to be applied for the production of compounds of formula (I) wherein Am is the group of the formula:

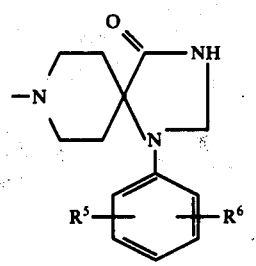

comprises reacting a compound of the formula:

(VIII)

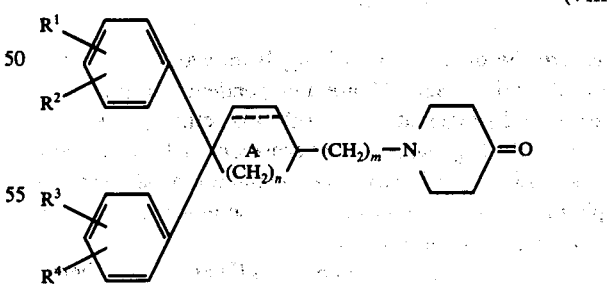

with a compound of the formula:

(IX)

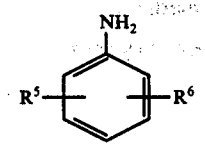

in an inert solvent such as water, acetic acid or methanol at 0° C to 100° C for 1 to 48 hours, and subjecting to hydrolysis the resulting compound of the formula:

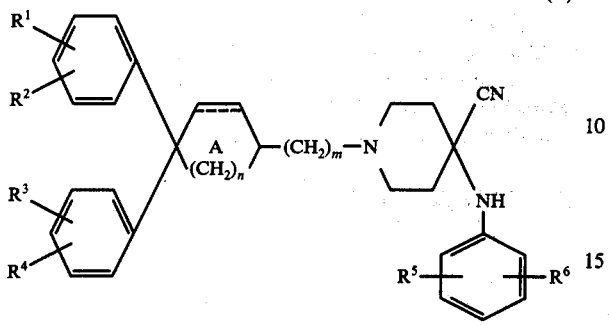
(X)

in the presence of a catalyst, preferably hydrochloric acid, sulfuric acid, sodium hydroxide or potassium hydroxide, at 0° C to 150° C for 10 minutes to 24 hours, and then subjecting to ring closure the resulting compound of the formula:

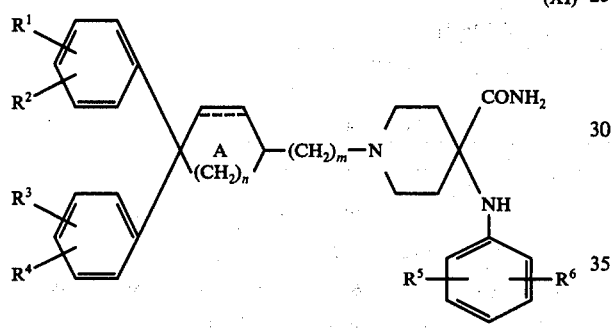
(XI)

in the presence of a condensing agent, preferably formamide or an aqueous solution of formaldehyde, at 100° C to 250° C for 1 to 48 hours.

In the above formulas, $R^1$, $R^2$, $R^3$, $R^4$, $R^5$, $R^6$, $n$, $m$ and the dotted line in Ring A are as defined above, and M is an alkali metal (e.g. K or Na).

METHOD V

This method, to be applied for the production of compounds of formula (I) wherein Am is the group of the formula:

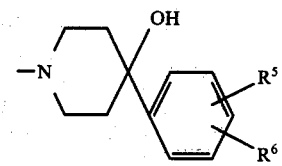

comprises reacting a compound of the formula:

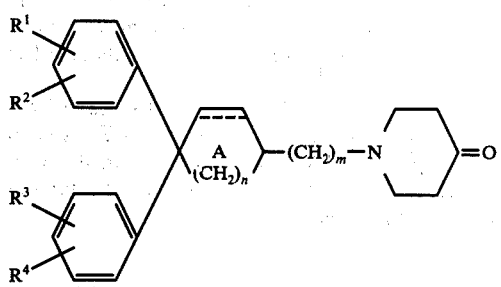
(VIII)

with a compound of the formula:

(XII)

in an inert solvent, preferably ether, tetrahydrofuran or dioxane, at −30° C to 150° C for 0.5 to 10 hours.

In the above formulas, $R^1$, $R^2$, $R^3$, $R^4$, $R^5$, $R^6$, $n$, $m$ and the dotted line in Ring A are as defined above, and Y is —Mg-Hal (Hal is a halogen atom) or Li.

The starting compounds of formulas (II) and (IV) wherein, for example, $n$ is 2 and $m$ is 0 can be prepared by such a conventional method as described in the following reaction scheme:

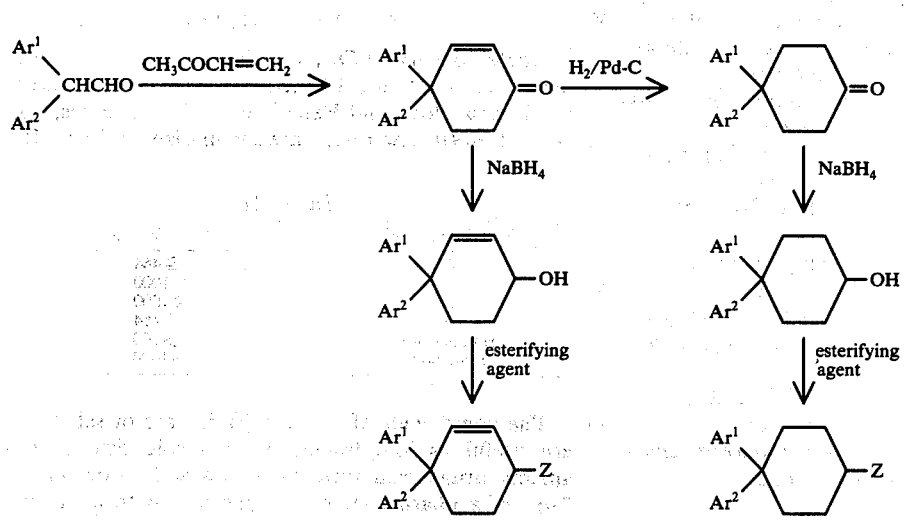

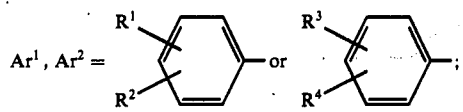

esterifying agent = $PCl_5$, $p\text{-}CH_{Cl, CH_3}SO_2Cl$, etc.

The compounds of formula (I), in case Ring A is cyclohexane ring, cyclopentene ring or cyclopentane ring, are optically active compounds or racemic modifications, which, if desired, can be separated in a conventional manner each into two enantiomers.

The compounds of formula (I) can be converted into acid addition salts with various inorganic and organic acids (e.g. hydrochloric, hydrobromic, sulfuric, nitric, phosphoric, maleic, fumaric, succinic, citric, or tartaric acid), and also into quaternary ammonium salts with dimethyl sulfate, diethyl sulfate, methyl iodide, ethyl bromide, etc.

The compounds of formula (I) and salts thereof exhibit potent and long-lasting psychotropic effects such as anti-apomorphine effect, effect on conditioned avoidance response, anti-methamphethamine effect, taming effect and analgesic effect.

The test was performed essentially by the method described by Paul A. J. Janssen et al. in "Arzneimittel-Forschung", vol. 17, 841 (1967), using groups of 5-7 female rats. The results are summarized in Table I.

Table I

| Test Compound | $ED_{50}$ mg/kg, p.o. |
|---|---|
| A | 2.46 |
| B | 0.10 |
| C | 0.18 |
| D | 0.51 |
| E | 0.28 |
| F | 0.14 |
| G | 0.17 |
| Haloperidol | 0.50 |
| Pimozide | 0.25 |

Anti-apomorphine effect was examined in respect of its durability at a dose of $ED_{50}$ value obtained by the above method. The results are summarized in Table II.

Table II

| Test Compound ($ED_{50}$ mg/kg) | Inhibition (%) | | | | | | | | | |
|---|---|---|---|---|---|---|---|---|---|---|
| hr | 1 | 3 | 6 | 18 | 24 | 48 | 72 | 96 | 120 | 144 |
| A (2.46) | 7.1 | | 21.4 | | 57.1 | 35.7 | 28.6 | 0 | | |
| B (0.10) | | | | | | 50.0 | 50.0 | 35.7 | 14.3 | 7.1 |
| C (0.18) | 14.3 | | | 50.0 | 64.3 | 64.3 | 64.3 | 35.7 | 21.4 | 0 |
| D (0.51) | 21.4 | | 50.0 | 71.4 | 71.4 | 64.3 | 71.4 | 71.4 | 64.3 | 35.7 |
| E (0.28) | 0 | 21.4 | | | 50.0 | 50.0 | 50.0 | 35.7 | 7.1 | |
| F (0.14) | | | 10.0 | | 50.0 | | | 20.0 | | 10.0 |
| G (0.17) | | | 20.0 | | 50.0 | | | 40.0 | | 10.0 |
| Haloperidol (0.50) | 57.1 | 50.0 | 21.4 | 14.3 | 7.1 | | | | | |
| Pimozide (0.25) | | | 57.1 | 50.0 | 35.7 | 7.1 | | | | |

ANTI-APOMORPHINE EFFECT

Test Compounds

A: 1-[4,4-bis(p-fluorophenyl)cyclohexyl]-4-(4-chloro-3-trifluoromethylphenyl)-4-piperidinol hydrochloride
B: 8-[4,4-bis(p-fluorophenyl)cyclohexyl]-1-(p-fluorophenyl)-1,3,8-triazaspiro[4.5]decan-4-one
C: 1-[1-(4,4-bis(p-fluorophenyl)cyclohexyl)-4-piperidyl]-5-chloro-2-benzimidazolinone
D: 1-[1-(4,4-bis(p-fluorophenyl)-2-cyclohexenyl)-4-piperidyl]-5-chloro-2-benzimidazolinone
E: 8-[4,4-bis(p-fluorophenyl)cyclohexyl]-1-(p-chlorophenyl)-1,3,8-triazaspiro[4.5]decan-4-one
F: 1-[1-(4,4-bis(p-fluorophenyl)cyclohexyl)-4-piperidyl]-5-fluoro-2-benzimidazolinone
G: 1-[1-(4,4-bis(p-fluorophenyl)-2-cyclohexenyl)-4-piperidyl]-5-fluoro-2-benzimidazolinone hydrochloride hemihydrate
Haloperidol (comparison): 1-[3-(p-fluorobenzoyl)-propyl]-4-(p-chlorophenyl)-4-piperidinol
Pimozide (comparison): 1-[1-(4,4-bis(p-fluorophenyl)-butyl)-4-piperidyl]-2-benzimidazolinone
Method and Results The data in Table II show the compounds of the invention exhibit more long-lasting action than Haloperidol and Pimozide.

ACUTE TOXICITY

Acute toxicity ($LD_{50}$, female mouse, per os) was measured by Litchfield-Wilcoxon method (The Journal of Pharmacology and Experimental Therapeutics, vol. 96, 99 (1949)). The results are summarized in Table III.

Table III

| Test Compound | $LD_{50}$ mg/kg |
|---|---|
| A | ≧464 |
| C | >1000 |
| D | ≧1000 |
| E | ≧464 |
| Haloperidol | >100 |
| Pimozide | >1000 |

The compounds of formula (I), in base or salt form, are useful as long-lasting psychotropic drugs, anti-anxiety drugs, sedatives, analgesics and so on, in the form of a pharmaceutical preparation with a suitable and conventional pharmaceutically acceptable carrier, without adversely affecting the patients.

The pharmaceutical preparations can take any conventional form such as tablets, capsules, granules, powders or injectable solutions.

FORMULATION EXAMPLES

The following is an example of formulations when a compound of the invention is administered for pharmaceutical purposes:

(a) Tablets are prepared from the following compositions:

|  | 5 mg Tablets | 25 mg Tablets | 50 mg Tablets |
|---|---|---|---|
| Compound (I) or its salt | 5 mg | 25 mg | 50 mg |
| Lactose | 43.6 | 58.6 | 51.4 |
| Microcrystalline Cellulose | 25.0 | 25.0 | 30.0 |
| Corn Starch | 20.0 | 30.0 | 30.0 |
| Methyl Cellulose | 0.4 | 0.4 | 0.6 |
| Talc | 6.0 | 6.0 | 8.0 |
| Total | 100 mg | 145 mg | 170 mg |

(b) Injectable solutions (5 mg/2 ml) are prepared from the following compositions:

| Compound (I) or its salt | 0.25% |
|---|---|
| Benzyl alcohol | 2.0 |
| Propylene glycol | 30.0 |
| Sodium chloride | 0.9 |
| Water for Injection | a sufficient amount to make 2 ml |

The dose of compound (I) or a salt thereof for human adults usually ranges from 2.5 to 50 mg per week for oral administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

A mixture of 4.1 g of 4,4-diphenylcyclohexyl tosylate, 2.2 g of 4-piperidyl-2-benzimidazolinone, 1.5 g of potassium carbonate, 1.5 g of potassium iodide and 50 ml of dimethylformamide is stirred at 55° C for 47 hours. The reaction mixture is cooled to room temperature and poured into ice water. The precipitate is collected by filtration and dissolved in chloroform under warming. The solution is washed with water and dried over sodium sulfate, and the chloroform is removed under reduced pressure. To the residue is added ether, and the mixture is cooled. The precipitated crystals are collected by filtration and recrystallized twice from a mixture of methanol and chloroform. The crystals are dried at 100° C under reduced pressure for many hours, because the solvent is not easily removable. Thus is obtained 1-[1-(4,4-diphenylcyclohexyl)-4-piperidyl]-2-benzimidazolinone as light gray crystals, melting at 289°–293° C.

EXAMPLE 2

A mixture of 13.5 g of 3,3-bis(p-fluorophenyl)cyclopentyl tosylate ($n_D^{20}$ 1.5691), 7.5 g of 1-(4-piperidyl)-5-chloro-2-benzimidazolinone hydrochloride, 8.6 g of potassium carbonate and 70 ml of dimethylformamide is stirred at 70° C for 52 hours. The reaction mixture is poured into ice water, and the aqueous layer is removed by decantation. The precipitated semi-solid is dissolved in chloroform. The solution is washed with water and dried over sodium sulfate, and the solvent is removed. The crude crystals are recrystallized from a mixture of chloroform and ethanol (20:1) to give 1-[1-(3,3-bis(p-fluorophenyl)cyclopentyl)-4-piperidyl]-5-chloro-2-benzimidazolinone as white crystals, melting at 131°–134° C.

EXAMPLE 3

A mixture of 11 g of 4,4-bis(p-fluorophenyl)cyclohexyl tosylate, 6 g of 1-(4-piperidyl)-5-chloro-2-benzimidazolinone, 3.5 g of potassium carbonate, 4.1 g of potassium iodide and 80 ml of dimethylformamide is stirred at 70°–80° C for 64 hours. The reaction mixture is poured into water, ether is added to the separated semi-solid, and the whole is stirred for 30 minutes. The substance insoluble in water and ether is collected by filtration, washed with ether and dried. The obtained crystals are dissolved in a mixture of chloroform and methanol (9:1), and the solution is concentrated to some degree and cooled. The precipitated crystals are collected by filtration and purified in the same manner to give 1-[1-(4,4-bis(p-fluorophenyl)cyclohexyl)-4-piperidyl]-5-chloro-2-benzimidazolinone as white crystals, melting at 279°–284° C.

EXAMPLE 4

A mixture of 6.1 g of 4,4-bis(p-fluorophenyl)-1-chloro-2-cyclohexene (m.p. 39°–42° C), 5.0 g of 1-(4-piperidyl)-5-chloro-2-benzimidazolinone, 2.8 g of potassium carbonate, 3.3 g of potassium iodide and 50 ml of dimethylformamide is stirred at 65°–70° C for 3 hours. The reaction mixture is poured into water, and the precipitated powder is collected by filtration, dried and dissolved in a mixture of chloroform and methanol (9:1). The solvent is then removed, and the precipitate is collected by filtration and purified in the same manner to give 1-[1-(4,4-bis(p-fluorophenyl)-2-cyclohexenyl)-4-piperidyl]-5-chloro-2-benzimidazolinone as white crystalline powder, melting at 153°–157° C. This white crystalline powder, when recrystallized from a mixture of ethanol and methanol (7:3), turns into white crystals showing a melting point of 217°–219° C.

EXAMPLE 5

A mixture of 6.1 g of 4,4-bis(p-fluorophenyl)-1-chloro-2-cyclohexene, 4.4 g of 1-(1,2,3,6-tetrahydro-4-pyridyl)-2-benzimidazolinone, 4.4 g of potassium carbonate and 50 ml of dimethylformamide is stirred at 55°–60° C for 4 hours. The reaction mixture is poured into water, and the aqueous mixture is extracted with chloroform. The extract is washed with water and dried over sodium sulfate, and the solvent is removed. The residual oil is purified by column chromatography on silica gel using a mixture of chloroform and methanol (9:1) as an eluent. The purified product (base) is converted in a conventional manner into the hydrochloride, and the hydrochloride thus obtained is again converted into the base. The solid (base) is recrystallized from a mixture of acetone and methanol to give 1-[1-(4,4-bis(p-fluorophenyl)-2-cyclohexenyl)-1,2,3,6tetrahydro-4-pyridyl]-2-benzimidazolinone as white crystals, melting at 200°–202°– C.

EXAMPLE 6

A mixture of 10 g of 4,4-bis(p-fluorophenyl)cyclohexanone, 6.6 g of 1-(4-piperidyl)-2-benzimidazolinone, 0.2 g of p-toluenesulfonic acid and 80 ml of xylene is stirred under reflux for 34 hours, the water formed being removed. The xylene is then removed under reduced pressure, and to the residue is added 200 ml of methanol and 10 ml of water. To the resulting mixture is added dropwise 15 g of sodium borohydride at about 20° C with cooling. After the addition is complete, the mixture is stirred under reflux for 3 hours. The reaction mixture is concentrated completely under reduced pressure, water is added to the residue, and the aqueous mixture is extracted with chloroform. The extract is washed with water and dried over sodium sulfate, and the solvent is removed. The residual viscous oil is purified by column chromatography using methylene chloride and then a mixture of methylene chloride and methanol (9:1) as an eluent. Thus is obtained 1-[1-(4,4-bis(p-fluorophenyl)cyclohexyl)-4-piperidyl]-2-benzimidazolinone as colorless crystals, melting at 235°-238° C.

EXAMPLE 7

A solution of 8.6 g of methyl 1-[4,4-bis(p-fluorophenyl)cyclohexyl]-4-oxo-3-piperidinecarboxylate (its oxalate monohydrate: m.p. 122°-126° C) in 40 ml of xylene is added dropwise to a solution of 2.2 g of o-phenylenediamine in 50 ml of xylene under reflux for 7 hours. During the addition about 40 ml of the solvent (equal amount of the addition) is removed over 7 hours. After the addition is complete, the resulting mixture is stirred under reflux for 3 hours. After cooling the solvent is removed under reduced pressure, and the residual oil is dissolved in ethanol and cooled. The precipitated crystals are collected by filtration and recrystallized from a mixture of methanol and ethanol to give 1-[1-(4,4-bis(p-fluorophenyl)cyclohexyl)-1,2,3,6-tetrahydro-4-pyridyl]-2-benzimidazolinone as white crystals, melting at 235°-238° C.

EXAMPLE 8

A mixture of 3.7 g of 4,4-bis(p-fluorophenyl)-1-chloro-2-cyclohexene, 3.1 g of 1-(p-bromophenyl)-1,3,8-triazaspiro[4.5]decan-4-one (m.p. 204°-207° C), 1.7 g of potassium carbonate, 2 g of potassium iodide and 25 ml of dimethylformamide is stirred at 65°-75° C for 3.5 hours. The reaction mixture is then poured into water. The precipitated powder is collected by filtration and dissolved in methanol. The solution is concentrated to some degree, and acetone is added thereto, and the whole mixture is cooled. The precipitated crystals are collected by filtration and purified in the same manner to give 8-[4,4-bis(p-fluorophenyl)-2-cyclohexenyl]-1-(p-bromophenyl)-1,3,8-triazaspiro[4.5]decan-4-one as white crystals, melting at 219°-221° C.

EXAMPLE 9

A mixture of 16 g of 4,4-bis(p-fluorophenyl)cyclohexyl mesylate, 10 g of 1-(p-fluorophenyl)-1,3,8-triazaspiro[4.5]decan-one (m.p. 234°-234.5° C), 6.1 g of potassium carbonate, 7.3 g of potassium iodide and 100 ml of dimethylformamide is stirred at 70°-80° C for 50 hours. The reaction mixture is poured into water, isopropyl ether is added to the aqueous mixture, and the resulting mixture is stirred for some time. The precipitated crystals are collected by filtration and dissolved in a mixture of chloroform and methanol (9:1). The solvent is removed to some degree and cooled in an ice bath. The precipitated crystals are collected by filtration and purified in the same manner to give 8-[4,4-bis(p-fluorophenyl)cyclohexyl]-1-(p-fluorophenyl)-1,3,8-triazaspiro[4.5]decan-4-one as white crystals, melting at 237°-240° C.

EXAMPLE 10

A mixture of 10.6 g of 4,4-bis(p-fluorophenyl)cyclohexyl tosylate, 5.7 g of 1-(3-chloro-4-fluorophenyl)-1,3,8-triazaspiro[4.5]decan-4-one (m.p. 194.5°-196.5° C), 3.3 g of potassium carbonate, 4 g of potassium iodide and 50 ml of dimethylformamide is stirred at 75°-80° C for 5 hours. The reaction mixture is poured into water, and the precipitated crystals are collected by filtration, dried in a desiccator and dissolved in a mixture of chloroform and methanol (9:1). The solution is concentrated to some degree and cooled. The precipitated crystals are collected by filtration and purified in the same manner to give 8-[4,4-bis(p-fluorophenyl)cyclohexyl]-1-(3-chloro-4-fluorophenyl)-1,3,8-triazaspiro[4.5]decan-4-one as white crystals, melting at 201°-203° C.

EXAMPLE 11

A mixture of 8.85 g of 4,4-bis(p-fluorophenyl)cyclohexyl tosylate, 4.5 g of 1-(p-chlorophenyl)-1,3,8-triazaspiro[4.5]decan-4-one, 2.8 g of potassium carbonate, 3.3 g of potassium iodide and 50 ml of dimethylformamide is stirred at 70°-75° C for 72 hours. The reaction mixture is poured into water, and the precipitated powder is collected by filtration and dried. The powder is dissolved in a mixture of chloroform and methanol (9:1), and the solvent is concentrated. The precipitated crystals are collected by filtration and purified in the same manner to give 8-[4,4-bis(p-fluorophenyl)cyclohexyl]-1-(p-chlorophenyl)-1,3,8-trazaspiro[4.5]decan-4-one as white crystals, melting at 258°-261° C.

EXAMPLE 12

A solution of 2.9 g of potassium cyanide in 8 ml of water is added dropwise to a mixture of 16.3 g of 1-[4,4-bis(p-fluorophenyl)cyclohexyl]-4-piperidone (oil; its hydrochloride: m.p. 214°-217° C), 4.1 g of aniline and 40 ml of acetic acid at room temperature with stirring. The resulting mixture is stirred at room temperature for 6 hours and allowed to stand at room temperature overnight. The reaction mixture is poured into ice water, the aqueous mixture is made alkaline with potassium carbonate, and the alkaline mixture is extracted with chloroform. The extract is washed with water and dried over sodium sulfate, and the solvent is removed. The residual oil is dissolved in acetone, and 20% ethanolic hydrochloric acid is added thereto. After cooling the precipitated hydrochloride is collected by filtration and converted in a conventional manner into the base. The obtained crystals are recrystallized from a mixture of acetone and petroleum ether to give 1-[4,4-bis(p-fluorophenyl)cyclohexyl]-4-cyano-4-anilinopiperidine as white crystals, melting at 139°-140° C.

To 16.5 g of 1-[4,4-bis(p-fluorophenyl)cyclohexyl]-4-cyano-4-anilinopiperidine is added gradually a solution of 180 g of concentrated sulfuric acid and 20 ml of water under cooling. After the addition is complete, the resulting mixture is stirred at 70° C for 1 hour and then cooled. The reaction mixture is poured into water, and the precipitated powder is collected by filtration. Then water is added to the powder, the aqueous mixture is made alkaline with potassium carbonate, and the alkaline solution is extracted with chloroform. The extract is washed with water and dried over sodium sulfate, and the solvent is removed. The precipitated crystals are collected by filration and recrystallized from a mixture of chloroform and acetone to give 1-[4,4-bis(p-fluorophenyl)cyclohexyl]-4-carbamoyl-4-anilinopiperidine as white crystals, melting at 224°–227° C.

To 16 g of 1-[4,4-bis(p-fluorophenyl)cyclohexyl]-4-carbamoyl-4-anilinopiperidine is added 30 g of formamide, the temperature is raised slowly, and the mixture is heated at 170° C for 14 hours. After cooling water is added to the reaction mixture, and the aqueous mixture is extracted with chloroform. The extract is washed with water and dried over sodium sulfate, and the solvent is removed. The precipitated crystals are collected by filtration and recrystallized from chloroform to give 8-[4,4-bis(p-fluorophenyl)cyclohexyl]-1-phenyl-1,3,8-triazaspiro[4.5]decan-4-one as white crystals, melting at 249°–253° C.

EXAMPLE 13

A mixture of 4.1 g of 4,4-diphenylcyclohexyl tosylate, 2.8 g of 4-(4-chloro-3-trifluoromethylphenyl)-4-piperidinol, 1.1 g of sodium carbonate and 400 ml of toluene is stirred under reflux for 48 hours. The reaction mixture is concentrated completely under reduced pressure, water is added to the residue, and the aqueous mixture is extracted with chloroform. The extract is washed with water and dried over sodium sulfate, and the solvent is removed. The esidual viscous oil is purified by column chromatography on silica gel using chloroform and then chloroform - methanol (9:1) as an eluent. The purified base is converted in a conventional manner into the hydrochloride. Thus is obtained 1-(4,4-diphenylcyclohexyl)-4-(4-chloro-3-trifluoromethylphenyl)-4-piperidinol hydrochloride monohydrate as white crystals, melting at 270°–273° C.

EXAMPLE 14

A mixture of 14.3 g of 4,4-bis(p-fluorophenyl)cyclohexanone, 14 g of 4-(4-chloro-3-trifluoromethylphenyl)-4-piperidinol, 0.5 g of p-toluenesulfonic acid and 100 ml of toluene is stirred under reflux for 145 hours, water formed being removed as an azeotropic mixture with toluene. The toluene is then removed, and the residual oil is dissolved in 100 ml of 90% methanol. To the solution is added slowly 19 g of sodium borohydride under cooling. After the addition is complete, the methanol is removed under reduced pressure, water is added to the residue, and the aqueous mixture is extracted with chloroform. The extract is washed with water and dried over sodium sulfate. The residual oil is purified by column chromatography on silica gel using a mixture of chloroform and methanol (9:1) as an eluent. The objective base thus obtained is converted in a conventional manner into the hydrochloride. Thus is obtained 1-[4,4-bis(p-fluorophenyl)cyclohexyl]-4-(4-chloro-3-trifluoromethylphenyl)-4-piperidinol hydrochloride as colorless crystals, melting at 274°–277° C.

EXAMPLE 15

A solution of 6.3 g of 3-trifluoromethyl-4-chloro-1-bromobenzene in 16 ml of tetrahydrofuran is added dropwise to a mixture of 0.6 g of magnesium turnings, a few crystals of iodine and 5 ml of tetrahydrofuran at room temperature with stirring by occasional cooling. After refluxing for 30 minutes, to the cooled Grignard reagent is added dropwise a solution of 7.3 g of 1-[4,4-bis(p-fluorophenyl)-2-cyclohexenyl]-4-piperidone (m.p. 112°–114° C) in 25 ml of tetrahydrofuran by occasional cooling. After the addition is complete, the resulting mixture is stirred at room temperature for 1 hour and then under reflux for an additional hour. After cooling a saturated aqueous solution of ammonium chloride is added dropwise to the reaction mixture, and the whole is extracted with ethyl acetate. The extract is washed with water and dried over sodium sulfate, and the solvent is removed. The residual oil is dissolved in acetone. To the acetone solution is added 20% ethanolic hydrochloric acid, and the whole is cooled. The precipitated crystals are collected by filtration and recrystallized from a mixture of methanol and acetone to give 1-[4,4-bis(p-fluorophenyl)-2-cyclohexenyl]-4-(4-chloro-3-trifluoromethylphenyl)-4-piperidinol hydrochloride as white crystals, melting at 252°–254° C.

Using the procedure set forth in the above examples, the following compounds are also producible:

16. 1-[1-(4,4-bis(p-tolyl)-2-cyclohexenyl)-4-piperidyl]-5-chloro-2-benzimidazolinone, m.p. 151°–153° C
17. 1-[1-(3,3-bis(p-fluorophenyl)cyclopentylmethyl)-4-piperidyl]-5-chloro-2-benzimidazolinone, m.p. 203°–206° C
18. 1-[1-(4,4-bis(p-fluorophenyl)-2-cyclohexenyl)-4-piperidyl]-2-benzimidazolinone hydrochloride, m.p. 213°–215° C
19. 1-[1-(4,4-bis(p-chlorophenyl)-2-cyclohexenyl)-4-piperidyl]-2-benzimidazolinone hydrochloride, m.p. 268°–272° C
20. 1-[1-(4,4-bis(p-chlorophenyl)cyclohexyl)-4-piperidyl]-2-benzimidazolinone, m.p. 256°–261° C
21. 1-[1-(3,3-bis(p-fluorophenyl)cyclopentyl)-4-piperidyl]-2-benzimidazolinone, m.p. 142°–145° C
22. 1-[1-(4,4-bis(p-tolyl)-2-cyclohexenyl)-4-piperidyl]-2-benzimidazolinone, m.p. 218°–220° C
23. 1-[1-(4,4-bis(p-fluorophenyl)cyclohexyl)-4-piperidyl]-5-fluoro-2-benzimidazolinone, m.p. 256°–259° C
24. 1-[1-(4,4-bis(p-fluorophenyl)-2-cyclohexenyl)-4-piperidyl]-5-fluoro-2-benzimidazolinone hydrochloride hemihydrate, m.p. 257°–259° C
25. 8-[4,4-bis(p-chlorophenyl)-2-cyclohexenyl]-1-phenyl-1,3,8-triazaspiro[4.5]decan-4-one, m.p. 217°–220° C; its hydrochloride; m.p. 257°–260° C
26. 8-[4,4-bis(p-fluorophenyl)cyclohexyl]-1-(2,4-difluorophenyl)-1,3,8-triazaspiro[4.5]decan-4-one, m.p. 214°–217° C; its hydrochloride: m.p. 274°–276° C
27. 8-[4,4-bis(p-fluorophenyl)-2-cyclohexenyl]-1-(3,4-dichlorophenyl)-1,3,8-triazaspiro[4.5]decan-4-one, m.p. 226°–227° C
28. 8-[4,4-bis(p-fluorophenyl)cyclohexyl]-1-(3,4-dichlorophenyl)-1,3,8-triazaspiro[4.5]decan-4-one, m.p. 241°–244° C
29. 8-[4,4-bis(p-fluorophenyl)cyclohexyl]-1-(p-bromophenyl)-1,3,8-triazaspiro[4.5]decan-4-one, m.p. 255°–259° C
30. 8-[4,4-bis(p-fluorophenyl)-2-cyclohexenyl]-1-(p-fluorophenyl)-1,3,8-triazaspiro[4.5]decan-4-one, m.p. 194°–196° C
31. 8-[4,4-bis(p-trifluoromethylphenyl)cyclohexyl]-1-phenyl-1,3,8-triazaspiro[4.5]decan-4-one hydrochloride, m.p. 268°–271° C
32. 8-[4,4-bis(p-fluorophenyl)-2-cyclohexenyl]-1-(p-chlorophenyl)-1,3,8-triazaspiro[4.5]decan-4-one, m.p. 266°–269° C
33. 8-[4,4-bis(p-fluorophenyl)-2-cyclohexenyl]-1-(3-chloro-4-fluorophenyl-1,3,8-triazaspiro[4.5]decan-4-one, m.p. 220°–221° C 34. 8-[4,4-bis(p-fluorophenyl)-2-cyclohexenyl]-1-phenyl-1,3,8-triazaspiro[4.5]decan-4-one, m.p. 193°-196° C
35. 8-[3,3-bis(p-fluorophenyl)cyclopentylmethyl]-1-(p-fluorophenyl)-1,3,8-triazaspiro[4.5]decan-4-one hydrochloride, m.p. 250°-253° C
36. 1-(4,4-diphenylcyclohexyl)-4-(p-chlorophenyl)-4-piperidinol, m.p. 187°-190° C
37. 1-[4,4-bis(p-fluorophenyl)cyclohexyl]-4-(p-tolyl)-4-piperidinol, m.p. 182°-183° C
38. 1-[4,4-bis(p-fluorophenyl)cyclohexyl]-4-(p-chlorophenyl)-4-piperidinol, m.p. 185°-189° C
39. 1-[4,4-bis(p-chlorophenyl)-2-cyclohexenyl]-4-(4-chloro-3-trifluoromethylphenyl)-4-piperidinol hydrochloride, m.p. 269°-271° C
40. 1-[4,4-bis(p-chlorophenyl)cyclohexyl]-4-(4-chloro-3-trifluoromethylphenyl)-4-piperidinol hydrochloride, m.p. 274°-276° C.
41. 1-[4,4-bis(p-tolyl)-2-cyclohexenyl]-4-(4-chloro-3-trifluoromethylphenyl)-4-piperidinol hydrochloride, m.p. 270°-271° C
42. 1-[3,3-bis(p-fluorophenyl)cyclopentyl]-4-(4-chloro-3-trifluoromethylphenyl)-4-piperidinol hydrochloride, m.p. 222°-225° C
43. 1-[1-(4,4-bis(3,4-difluorophenyl)cyclohexyl)-4-piperidyl]-5-chloro-2-benzimidazolinone, m.p. 265°-269° C
44. 1-[1-(4,4-bis(2,4-difluorophenyl)cyclohexyl)-4-piperidyl]-5-chloro-2-benzimidazolinone hydrochloride, m.p. 302°-305° C
45. 1-[1-(4,4-bis(2,4-difluorophenyl)-2-cyclohexenyl)-4-piperidyl]-5-chloro-2-benzimidazolinone hydrochloride, m.p. 251°-253° C
46. 8-[4,4-bis(3,4-difluorophenyl)-2-cyclohexenyl]-1-(p-fluorophenyl)-1,3,8-triazaspiro[4.5]decan-4-one, m.p. 209°-212° C
47. 1-[1-(4,4-bis(3,4-difluorophenyl)cyclohexyl)-4-piperidyl]-5-fluoro-2-benzimidazolinone
48. 1-[1-(4,4-bis(2,4-difluorophenyl)cyclohexyl)-4-piperidyl]-5-fluoro-2-benzimidazolinone
49. 1-[1-(4,4-bis(2,4-difluorophenyl)-2-cyclohexenyl)-4-piperidyl]-5-fluoro-2-benzimidazolinone
50. 1-[1-(4,4-bis(p-bromophenyl)cyclohexyl)-4-piperidyl]-5-chloro-2-benzimidazolinone
51. 1-[1-(4,4-bis(p-fluorophenyl)cyclohexyl)-4-piperidyl]-5,6-difluoro-2-benzimidazolinone
52. 1-[1-(4,4-bis(p-fluorophenyl)cyclohexyl)-4-piperidyl]-5-trifluoromethyl-2-benzimidazolinone
53. 1-[1-(4,4-bis(p-fluorophenyl)-2-cyclohexenyl)-4-piperidyl]-5-trifluoromethyl-2-benzimidazolinone
54. 1-[1-(4,4-bis(p-fluorophenyl)cyclohexyl)-4-piperidyl]-5,6-dichloro-2-benzimidazolinone
55. 1-[1-(4,4-bis(p-fluorophenyl)cyclohexyl)-4-piperidyl]-5-methyl-2-benzimidazolinone
56. 1-[1-(4,4-bis(p-fluorophenyl)cyclohexyl)-4-piperidyl]-5-bromo-2-benzimidazolinone
57. 8-[4,4-bis(3,4-difluorophenyl)cyclohexyl]-1-(p-fluorophenyl)-1,3,8-triazaspiro[4.5]decan-4-one
58. 8-[4,4-bis(2,4-difluorophenyl)cyclohexyl]-1-(p-fluorophenyl)-1,3,8-triazaspiro[4.5]decan-4-one
59. 8-[4,4-bis(2,4-difluorophenyl)cyclohexyl]-1-(p-chlorophenyl-1,3,8-triazaspiro[4.5]decan-4-one
60. 8-[4,4-bis(3,4-difluorophenyl)cyclohexyl]-1-(p-chlorophenyl)-1,3,8-triazaspiro[4.5]decan-4-one
61. 8-[4,4-bis(2,4-difluorophenyl)-2-cyclohexenyl]-1-(p-fluorophenyl)-1,3,8-triazaspiro[4.5]decan-4-one
62. 1-[4,4-bis(2,4-difluorophenyl)cyclohexyl]-4-(4-chloro-3-trifluoromethylphenyl)-4-piperidinol
63. 8-[4,4-bis(p-fluorophenyl)cyclohexyl]-1-(p-tolyl)-1,3,8-triazaspiro-[4.5]decan-4-one Although the present invention has been adequately discussed in the foregoing specification and examples included therein, one readily recognizes that various changes and modifications may be made without departing from the spirit and scope thereof.

What is claimed is:

1. A compound of the formula:

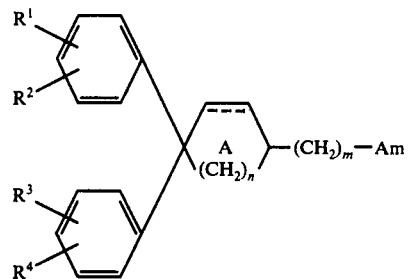

wherein:
the dotted line in Ring A indicates an optional bond;
$R^1$, $R^2$, $R^3$ and $R^4$ are independently a hydrogen atom, a halogen atom, a trifluoromethyl group or a lower alkyl group;
$n$ is 1 or 2;
$m$ is 0 or 1;
Am is a piperidino group of the formula:

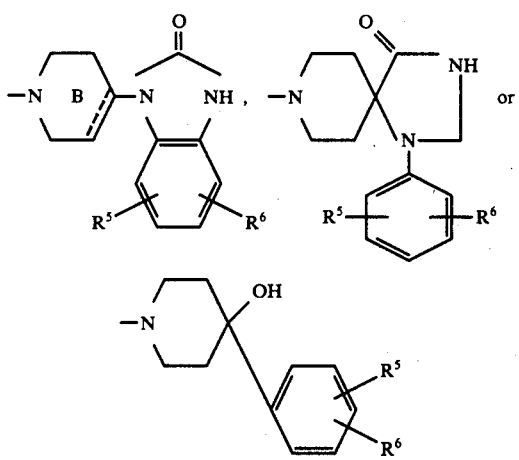

where the dotted line in Ring B indicates an optional bond; and
$R^5$ and $R^6$ are independently a hydrogen atom, a halogen atom, a trifluoromethyl group or a lower alkyl group;
and a pharmaceutically acceptable salt thereof.

2. A compound of the formula:

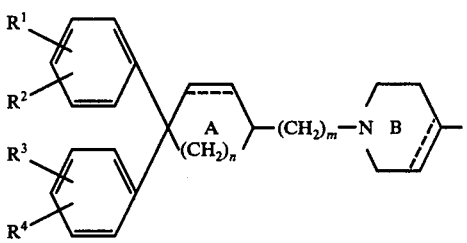

-continued

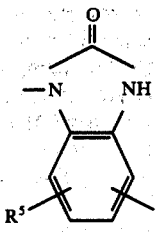

wherein the dotted line in each of Rings A and B indicates an optional bond; $R^1$, $R^2$, $R^3$, $R^4$, $R^5$ and $R^6$ are independently a hydrogen atom, a halogen atom, a trifluoromethyl group or a lower alkyl group; $n$ is 1 or 2; and $m$ is 0 or 1; and a pharmaceutically acceptable salt thereof.

3. The compound of claim 2 wherein $R^1$ is F, $R^2$ is H or F, $R^3$ is F, $R^4$ is H or F, $n$ is 2, and $m$ is 0.

4. The compound of claim 2 wherein $R^1$ is F at para-position, $R^2$ is H, $R^3$ is F at para-position, $R^4$ is H, $n$ is 2 and $m$ is 0.

5. The compound of claim 2: 1-[1-(4,4-diphenylcyclohexyl)-4-piperidyl]-2-benzimidazolinone.

6. The compound of claim 2: 1-[1-(3,3-bis(p-fluorophenyl)cyclopentyl)-4-piperidyl]-5-chloro-2-benzimidazolinone.

7. The compound of claim 2: 1-[1-(4,4-bis(p-fluorophenyl)cyclohexyl)-4-piperidyl]-5-chloro-2-benzimidazolinone.

8. The compound of claim 2: 1-[1-(4,4-bis(p-fluorophenyl)-2-cyclohexenyl)-4-piperidyl]-5-chloro-2-benzimidazolinone.

9. The compound of claim 2: 1-[1-(4,4-bis(p-fluorophenyl)-2-cyclohexenyl)-1,2,3,6-tetrahydro-4-pyridyl]-2-benzimidazolinone.

10. The compound of claim 2: 1-[1-(4,4-bis(p-fluorophenyl)cyclohexyl)-4-piperidyl]-2-benzimidazolinone.

11. The compound of claim 2: 1-[1-(4,4-bis(p-fluorophenyl)cyclohexyl)-1,2,3,6-tetrahydro-4-pyridyl]-2-benzimidazolinone.

12. The compound of claim 1: 8-[4,4-bis(p-fluorophenyl)-2-cyclohexenyl]-1-(p-bromophenyl)-1,3,8-triazaspiro[4.5]decan-4-one.

13. The compound of claim 1: 8-[4,4-bis(p-fluorophenyl)cyclohexyl]-1-(p-fluorophenyl)-1,3,8-triazaspiro-[4.5]decan-4-one.

14. The compound of claim 1: 8-[4,4-bis(p-fluorophenyl)cyclohexyl]-1-(3-chloro-4-fluorophenyl)-1,3,8-triazaspiro[4.5]decan-4-one.

15. The compound of claim 1: 8-[4,4-bis(p-fluorophenyl)cyclohexyl]-1-(p-chlorophenyl)-1,3,8-triazaspiro-[4.5]decan-4-one.

16. The compound of claim 1: 8-[4,4-bis(p-fluorophenyl)cyclohexyl]-1-phenyl-1,3,8-triazaspiro[4.5]decan-4-one.

17. The compound of claim 1: 1-(4,4-diphenylcyclohexyl)-4-(4-chloro-3-trifluoromethylphenyl)-4-piperidinol.

18. The compound of claim 1: 1-[4,4-bis(p-fluorophenyl)cyclohexyl]-4-(4-chloro-3-trifluoromethylphenyl)-4-piperidinol.

19. The compound of claim 1: 1-[4,4-bis(p-fluorophenyl)-2-cyclohexenyl]-4-(4-chloro-3-trifluoromethylphenyl)-4-piperidinol.

20. The compound of claim 2: 1-[1-(4,4-bis(p-tolyl)-2-cyclohexenyl)-4-piperidyl]-5-chloro-2-benzimidazolinone.

21. The compound of claim 2: 1-[1-(3,3-bis(p-fluorophenyl)cyclopentylmethyl)-4-piperidyl]-5-chloro-2-benzimidazolinone.

22. The compound of claim 2: 1-[1-(4,4-bis(p-fluorophenyl)-2-cyclohexenyl)-4-piperidyl]-2-benzimidazolinone.

23. The compound of claim 2: 1-[1-(4,4-bis(p-chlorophenyl)-2-cyclohexenyl)-4-piperidyl]-2-benzimidazolinone.

24. The compound of claim 2: 1-[1-(4,4-bis(p-chlorophenyl)cyclohexyl)-4-piperidyl]-2-benzimidazolinone.

25. The compound of claim 2: 1-[1-(3,3-bis(p-fluorophenyl)cyclopentyl)-4-piperidyl]-2-benzimidazolinone.

26. The compound of claim 2: 1-[1-(4,4-bis(p-tolyl)-2-cyclohexenyl)-4-piperidyl]-2-benzimidazolinone.

27. The compound of claim 2: 1-[1-(4,4-bis(p-fluorophenyl)cyclohexyl)-4-piperidyl]-5-fluoro-2-benzimidazolinone.

28. The compound of claim 2: 1-[1-(4,4-bis(p-fluorophenyl)-2-cyclohexenyl)-4-piperidyl]-5-fluoro-2-benzimidazolinone.

29. The compound of claim 1: 8-[4,4-bis(p-chlorophenyl)-2-cyclohexenyl]-1-phenyl-1,3,8-triazaspiro[4.5]-decan-4-one.

30. The compound of claim 1: 8-[4,4-bis(p-fluorophenyl)cyclohexyl]-1-(2,4-difluorophenyl)-1,3,8-triazaspiro[4.5]decan-4-one.

31. The compound of claim 1: 8-[4,4-bis(p-fluorophenyl)-2-cyclohexenyl]-1-(3,4-dichlorophenyl)-1,3,8-triazaspiro[4.5]decan-4-one.

32. The compound of claim 1: 8-[4,4-bis(p-fluorophenyl)cyclohexyl]-1-(3,4-dichlorophenyl)-1,3,8-triazaspiro[4.5]decan-4-one.

33. The compound of claim 1: 8-[4,4-bis(p-fluorophenyl)cyclohexyl]-1-(p-bromophenyl)-1,3,8-triazaspiro-[4.5]decan-4-one.

34. The compound of claim 1: 8-[4,4-bis(p-fluorophenyl)-2-cyclohexenyl]-1-(p-fluorophenyl)-1,3,8-triazaspiro[4.5]decan-4-one.

35. The compound of claim 1: 8-[4,4-bis(p-trifluoromethylphenyl)cyclohexyl]-1-phenyl-1,3,8-triazaspiro-[4.5]decan-4-one.

36. The compound of claim 1: 8-[4,4-bis(p-fluorophenyl)-2-cyclohexenyl]-1-(p-chlorophenyl)-1,3,8-triazaspiro[4.5]decan-4-one.

37. The compound of claim 1: 8-[4,4-bis(p-fluorophenyl)-2-cyclohexenyl]-1-(3-chloro-4-fluorophenyl)-1,3,8-triazaspiro[4.5]decan-4-one.

38. The compound of claim 1: 8-[4,4-bis(p-fluorophenyl)-2-cyclohexenyl]-1-phenyl-1,3,8-triazaspiro[4.5]-decan-4-one.

39. The compound of claim 1: 8-[3,3-bis(p-fluorophenyl)cyclopentylmethyl]-1-(p-fluorophenyl)-1,3,8-triazaspiro[4.5]decan-4-one.

40. The compound of claim 1: 1-(4,4-diphenylcyclohexyl)-4-(p-chlorophenyl)-4-piperidinol.

41. The compound of claim 1: 1-[4,4-bis(p-fluorophenyl)cyclohexyl]-4-(p-tolyl)-4-piperidinol.

42. The compound of claim 1: 1-[4,4-bis(p-fluorophenyl)cyclohexyl]-4-(p-chlorophenyl)-4-piperidinol.

43. The compound of claim 1: 1-[4,4-bis(p-chlorophenyl)-2-cyclohexenyl]-4-(4-chloro-3-trifluoromethylphenyl)-4-piperidinol.

44. The compound of claim 1: 1-[4,4-bis(p-chlorophenyl)cyclohexyl]-4-(4-chloro-3-trifluoromethylphenyl)-4-piperidinol.

45. The compound of claim 1: 1-[4,4-bis(p-tolyl)-2-cyclohexenyl]-4-(4-chloro-3-trifluoromethylphenyl)-4-piperidinol.

46. The compound of claim 1: 1-[3,3-bis(p-fluorophenyl)cyclopentyl]-4-(4-chloro-3-trifluoromethylphenyl)-4-piperidinol.

47. The compound of claim 1: 1-[1-(4,4-bis(3,4-difluorophenyl)cyclohexyl)-4-piperidyl]-5-chloro-2-benzimidazolinone.

48. The compound of claim 1: 1-[1-(4,4-bis(2,4-difluorophenyl)cyclohexyl)-4-piperidyl]-5-chloro-2-benzimidazolinone.

49. The compound of claim 1: 1-[1-(4,4-bis(2,4-difluorophenyl)-2-cyclohexenyl)-4-piperidyl]-5-chloro-2-benzimidazolinone.

50. The compound of claim 1: 8-[4,4-bis(3,4-difluorophenyl]-2-cyclohexenyl]-1-(p-fluorophenyl)-1,3,8-triazaspiro[4.5]decan-4-one.

51. A psychotropic composition comprising the compound of claim 2 in combination with a pharmaceutically acceptable inert carrier, said compound being present in a psychotropically effective amount.

52. A psychrotropic composition comprising the compound of claim 1 in combination with a pharmaceutically acceptable inert carrier, said compound being present in a psychotropically effective amount.

* * * * *